United States Patent
Oetjen

(12) 
(10) Patent No.: US 6,176,121 B1
(45) Date of Patent: Jan. 23, 2001

(54) METHOD OF DETERMINING RESIDUAL MOISTURE CONTENT DURING SECONDARY DRYING IN A FREEZE-DRYING PROCESS

(76) Inventor: Georg-Wilhelm Oetjen, Tondernstrasse 7, D-23556 Lübeck (DE)

( * ) Notice: Under 35 U.S.C. 154(b), the term of this patent shall be extended for 0 days.

(21) Appl. No.: 08/875,708

(22) PCT Filed: Aug. 18, 1995

(86) PCT No.: PCT/EP95/03294

§ 371 Date: Aug. 4, 1997

§ 102(e) Date: Aug. 4, 1997

(87) PCT Pub. No.: WO96/25654

PCT Pub. Date: Aug. 22, 1996

(30) Foreign Application Priority Data

Feb. 14, 1995 (DE) .............................................. 195 04 814
Feb. 5, 1996 (DE) .............................................. 196 04 044
Feb. 5, 1996 (DE) .............................................. 196 04 043

(51) Int. Cl.$^7$ .............................. G01N 25/56; G01N 5/02
(52) U.S. Cl. ........................................ 73/73; 73/74; 73/76
(58) Field of Search .................................... 73/74, 73, 76

(56) References Cited

U.S. PATENT DOCUMENTS

| 2,575,169 | * 11/1951 | Green ....................................... 73/73 |
| 4,142,403 | * 3/1979 | Lohnes et al. ........................... 73/76 |
| 4,168,623 | 9/1979 | Thomas, Jr. ............................. 73/76 |
| 4,506,994 | * 3/1985 | Scwab ..................................... 374/28 |
| 4,561,191 | 12/1985 | Parkinson ................................. 34/5 |
| 4,606,650 | 8/1986 | Harris ..................................... 374/14 |
| 4,709,579 | 12/1987 | Parker et al. ............................ 73/76 |
| 4,889,201 | 12/1989 | Oldendorf ......................... 177/25.14 |
| 5,280,678 | 1/1994 | Jennings ................................. 34/30 |

OTHER PUBLICATIONS

Swokowski, 1988, pp. 156, 260–262.*
Developments in Biological Standardization, vol. 36, 1977 BASEL (SW), Seiten 181–189, Jewell, et al.

* cited by examiner

*Primary Examiner*—Hezron Williams
*Assistant Examiner*—Dennis S Loo
(74) *Attorney, Agent, or Firm*—Fay, Sharpe, Fagan, Minnich & McKee, LLP

(57) ABSTRACT

A method for determining the residual moisture content during secondary drying in the dry product of a freeze-drying process is disclosed. In order to determine the residual moisture content without interruption of the drying process is suggested that the desorption rate is measured at certain intervals (for example 10 minutes) during the secondary drying phase. A computer calculates from two or several of these measured values the time at which a desorption rate would be reached (desorption rate zero point) which would alter the desired residual moisture by only a tolerably small amount. The respective residual moisture is determined by the computer by chronological integration of desorption rates from zero point until the moment of measurement taking.

12 Claims, 2 Drawing Sheets

METHOD OF DETERMINING RESIDUAL MOISTURE CONTENT DURING SECONDARY DRYING IN A FREEZE-DRYING PROCESS

BACKGROUND OF THE INVENTION

Freeze-drying is a method for removal of previously frozen water, for example from drugs and food. In general, the method is carried out at an air pressure which is low vis-a-vis the water vapor pressure at the selected temperature of the ice. For example, an ice temperature of −20° C. corresponds to a water vapor pressure (in equilibrium) of 1.03 mbar. In order for the water vapor to be able to flow from the surface of the ice into the drying chamber, the water vapor pressure in the drying chamber must be distinctly lower than 1.03 mbar, i.e. for example 0.4 mbar. According to the preceding statement, the air pressure must be low vis-a-vis 0.4 mbar, i.e. for example 0.05 mbar.

As long as there crystallized (frozen) water remains in the product, this drying segment is called the primary- or the sublimation drying. If, during this phase of drying, a shut-off device is closed for a short time (seconds) between chamber and condenser, there occurs in the chamber the equilibrium water vapor pressure which corresponds to the prevailing ice temperature. From the increase in pressure it is possible to draw a direct conclusion with respect to the ice temperature. This method is called barometric temperature measuring (BTM).

When there is no longer any water in the form of ice present, the remaining water is absorbed by the dry product or is more or less solidly bonded thereto. Removal of this water is called secondary or desorption drying. The desorbable water volume during this phase depends upon the temperature of the product, the type of water bond and the still present water volume. In the thermo-dynamic equilibrium, the respective water vapor pressure (for a given temperature) constitutes a measure for the water content of the dry product. This function: water vapor pressure as a function of water content of the dry product is called desorption isotherm. The establishment of this equilibrium takes, however,—depending upon temperature—on the order of hours. During a drying process which, in general, lasts only a few hours, it is not possible to repeatedly determine this measuring quantity. It is therefore customary to remove from the drying chamber, during the secondary drying, single bottles containing dry product or a specimen from the bulk product with a vacuum manipulator, to determine the residual moisture (RM) and to terminate the drying process upon reaching the desired RM. If such device is not available, it is necessary to run several batches, to select different drying times and to measure the proper RM. In that case one has to rely, however, on that the process cycle is always identically controlled. Certain deviations are hereby unavoidable, and it is always a risk to estimate which deviations are still tolerable and which are not.

In addition, both methods have the serious drawback that the RM can only be determined on the basis of several samples. As experience demonstrates, the RM values of several samples can substantially fluctuate, depending, for example, upon the location of the bottles or the location of the bulk product in the chamber. Therefore it is desirable to measure an average RM for all bottles (which may amount to a total of up to several thousands) or across the entire bulk product (which may amount up to several tons).

BRIEF DESCRIPTION OF THE DRAWINGS

Referring to the Figures.

DETAILED DESCRIPTION OF THE PREFERRED EMBODIMENT

According to the present invention, the "integral" RM-value can be determined at certain time intervals during the secondary drying without significant interruption of the drying process. In order to do this, one proceeds as follows: The shut-off device between chamber and condenser is closed for a certain time, for example 30 or 60 seconds. During the shut-off time, the desorbing water vapor permits the pressure to rise in the chamber.

It is possible to calculate the desorption rate (DR) or from the shut-off time, the chamber volume and the dry mass present in the chamber using the following equations shown below.

$$V \times \frac{(d_p)}{(d_t)} \text{ yields } \frac{1 \times \text{mbar}}{h}$$

where V=chamber volume, $d_p$=rise in pressure, $d_t$=measuring time

According to Avogadro's Hypothesis, 1×mbar can be converted into mass, (for example grams). The desorption rate (DR) is defined as follows:

$$DR = \frac{\text{Mass of desorbed water} \times 100}{\text{hours} \times \text{mass of dry substance}} \ [\%/h]$$

water in % of dry mass per hour

According to the present invention, it is possible, from two successive such measurements, to extrapolate the point in time at which the DR has reached a given small value. If this value is chosen so small, that it only tolerably influences the present residual moisture which is to be measured, then one can proceed from said thusly defined DR-value "DR-zero point" and chronologically integrate the DR values up to the more current measuring time point. The integrated DR-value is the desired DR the time of measuring.

Figure 1:
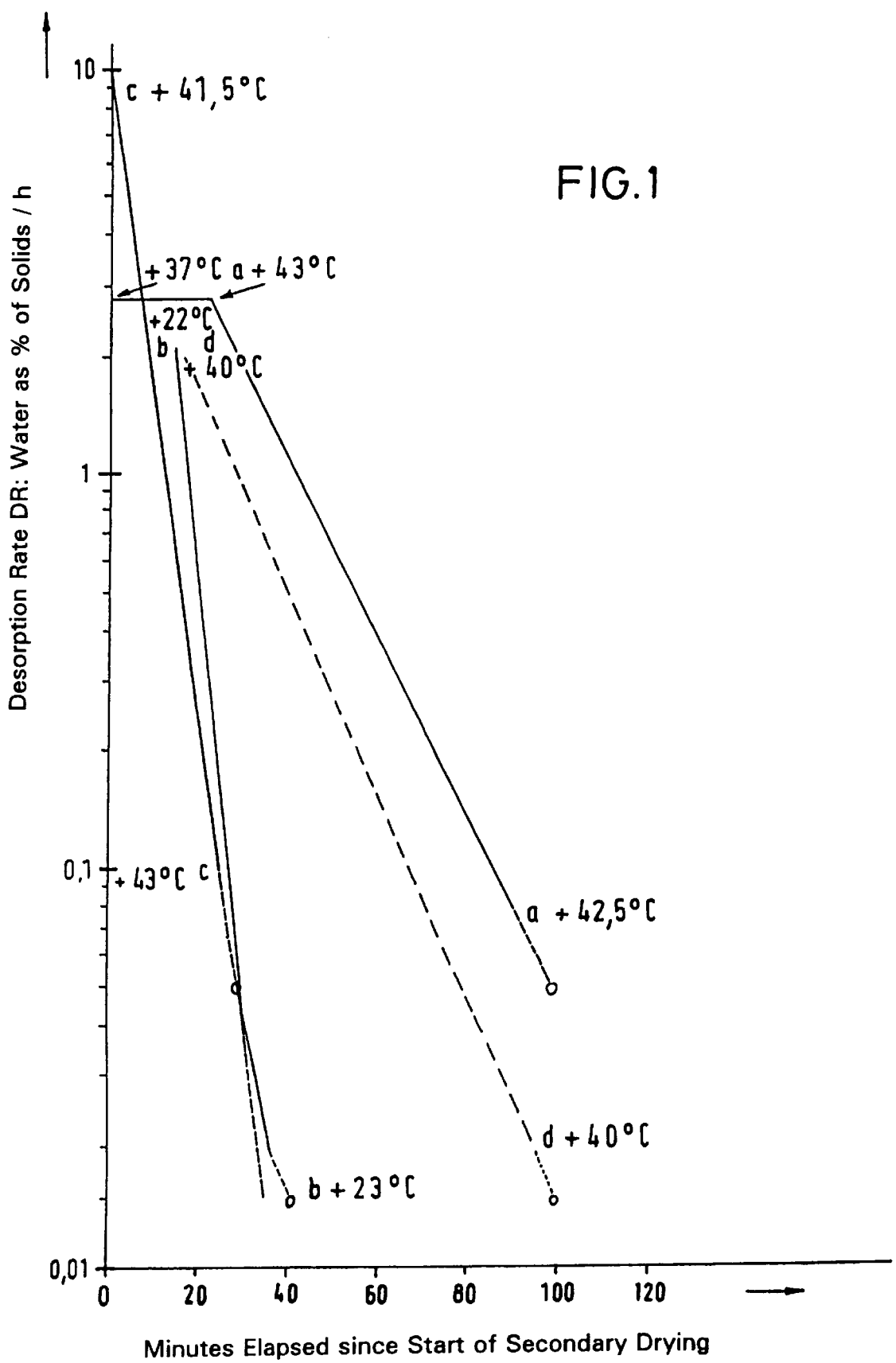
FIG. 1 is a graph illustrating the desorption rate (DR) (water in % of solid material/h) versus time (minutes since onset of secondary drying)

Referring to FIG. 1, the desorption rate of various products is shown. The desorption rate DR (Water in % of solid material/h) is recorded in FIG. 1 relationship to time (minutes since onset of secondary drying).

| | |
|---|---|
| Product a: | product temperature 37° C. to 42.5° C. |
| Product b: | product temperature 22° C. to 23° C. |
| Product c: | product temperature 41.5° C. to 43° C. |
| Product d: | product temperature 40° C. to 40° C. |

The respective DR zero point for integration of the residual moisture is marked with a small circle.

Products a and d are comparable, the primary drying of product d is controlled in such a manner that the primary drying time for d is shorter by approximately 15 minutes than the primary drying time for product a.

Inasmuch as the slope of the DR-curve (FIG. 1 curve a) undergoes a change in the transitional phase from the primary drying to the secondary drying, it is possible to determine the onset of the secondary drying phase: The extrapolated zero point of the DR-curve may still undergo only a minor change. Similar (conditions) may occur with very small DR's, which, normally, are no longer of any importance. If one intends to take these deviations into account (FIG. 1 curve b) one must, perhaps, correct the "zero point" when taking the last measurement. This applies specifically if there are minor changes in the temperature of the product during the secondary drying (FIG. 1 curve b).

Measuring each DR-value includes a certain imprecision, the effect of which can be minimized if, according to the invention, three successive measurements are taken and from these, according to the method of least squares, a determination is made of the most probable straight line. The "DR-zero point" used for integration then lies on this straight line.

Figure 2:
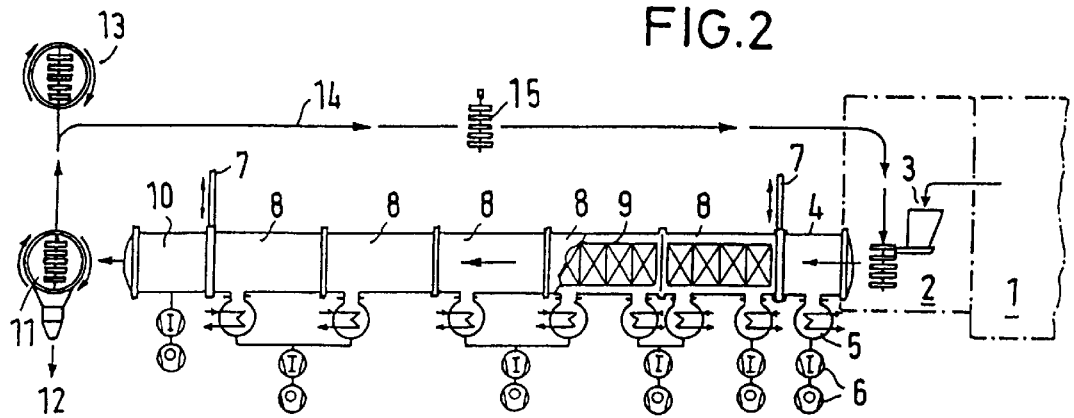
FIG. 2 is a schematic view of a continuous freeze-drying plant.

FIG. 2 illustrates a freeze-drying plant of the type for which the present invention can be used and, in this regard, is a continuous freeze-drying plant (System CQC by Messrs Leybold AG, Hanau). It comprises a freezing chamber 1; a loading chamber 2; a shell loader 3; an entry gate 4; a condenser 5; a pump aggregate 6 with one each rotary piston vacuum pump and one each roller piston vacuum pump; a slider (vacuum tight) 7; a freeze-drying tunnel 8; a heating plate system 9 with remote CQC-suspension car; an exit gate 10; an unloading station 11; a product discharge 12; a washing unit 13; a track system for car transport 14; and a CQC-suspension car 15.

The invention can be used in continuous freeze-drying plants (FIG. 2) if two (or three) pressure increase measurements are taken at the exit gate and from these, based on the calculated zero point, a conclusion is drawn with respect to the RM through integration.

If the product has too high a residual moisture at the exit gate 10, it is possible to lengthen the product transport and thus the drying time by one cycle period, or, if the RM is too low, to shorten the cycle period, beginning with the next transport step.

Figure 3:
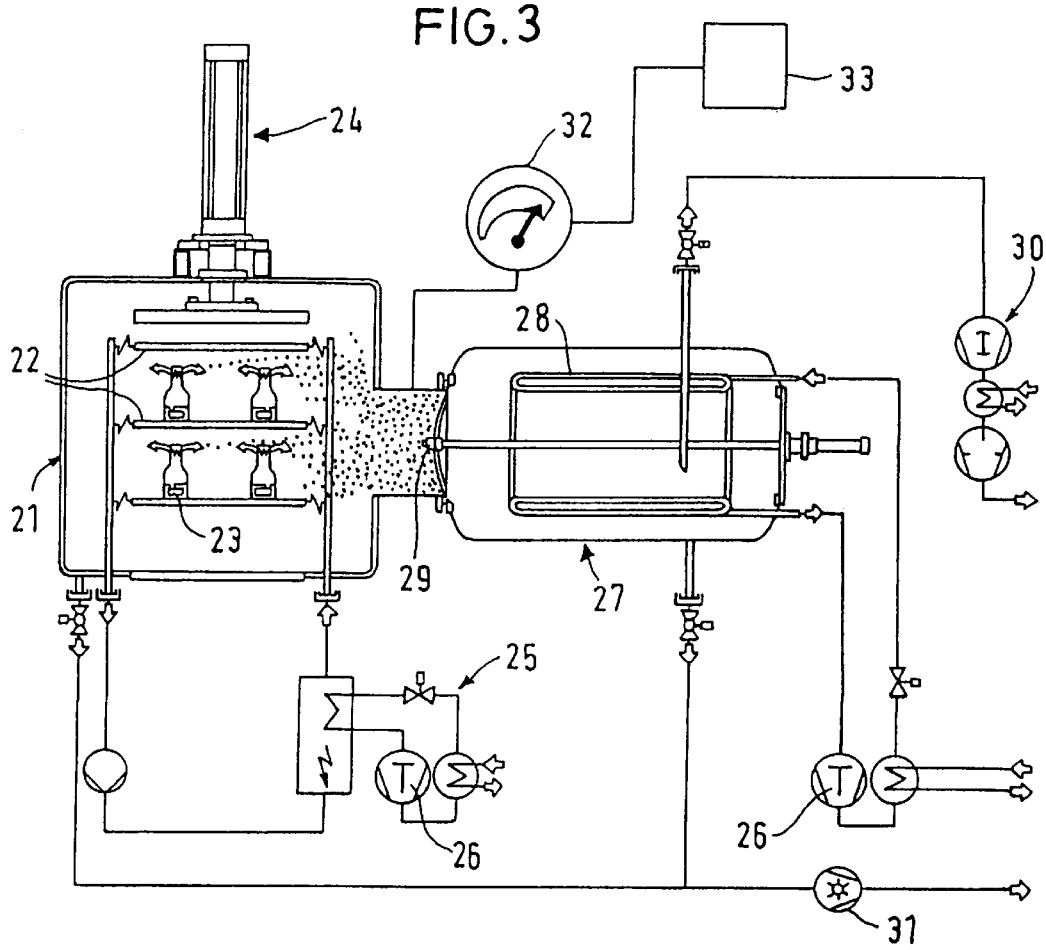
FIG. 3 is a schematic view of an intermittently operated freeze-drying plant.

FIG. 3 illustrates an intermittently operated freeze-drying plant, which is frequently utilized in the pharmaceutical industry, and comprises a freeze-drying chamber 21; adjustment plates 22; a container 23 with frozen-to be-dried product; closing equipment 24; a tempering circuit 25 (cooling/heating); refrigeration machines 26; a condenser 27; cooling medium evaporator 28; a shut-off valve 29; a vacuum pump stand 30; a transportation pump 31 for discharge of defrosting liquid and wash water; a pressure measuring instrument 32; and a computer 33.

Several methods are known to determine the residual moisture, which produce different results with different products, because each method includes, or no longer includes, certain kinds of bonded water. The method described here corresponds to the thermo-gravimetric method (see May J. C., etc.: Measurement of Final Container Residual Moisture in Freeze-Dried Biological Products: International Symposium on Biological Product Freeze-Drying and Formulation, Pages 153 to 164, Publisher: Karger-Verlag, Basel, 1991). The difference of the thermo-gravimetric method described by May is that the dry substance is not weighed with a scale until a practically constant weight is reached, but that the water vapor gives off is measured until the emission of water vapor is practically finished or has reached a desired value.

The invention has been described with reference to preferred and alternate embodiments. Obviously, modifications and alterations will occur to others upon the reading and understanding of this specification. It is intended to include all such modifications and alterations insofar as they come within the scope of the appended claims or the equivalents thereof.

Having thus described the preferred embodiments, the invention is claimed as follows:

1. A method for determining residual moisture content without a mass balance in a dry product from a freeze-drying process during secondary drying, the method comprising:
   (a) measuring a desorption rate during the secondary drying phase by measuring pressure at given intervals;
   (b) with a computer, from two or more of the measured desorption rates, calculating a target point in time, at which the desorption rate is projected to reach a target desorption rate which alters the desired residual moisture content by only a preselected amount;
   (c) determining the respective residual moisture with the computer by chronological integration of the desorption rates from the target time up to the time of taking the measurement of step (a).

2. A method for determining residual moisture content in dry product from a freeze-drying process during secondary drying, the method comprising:
   (a) tracking pressure rise measurements at intervals during the secondary drying phase;
   (b) determining desorption rates from the pressure rise measurements;
   (c) with a computer, from two or more of the determined desorption rates calculating a target point in time, at which the desorption rate is projected to reach a target desorption rate which alters the desired residual moisture content by only a preselected amount;
   (d) determining the target time for reaching the target desorption rate again after each pressure rise measurement taking and determining a corrected residual moisture content;
   (e) determining a current residual moisture with the computer by chronological integration of the determined desorption rates from the target time up to the time of taking each pressure rise measurement.

3. The method according to claim 1 wherein step (a) includes visual reading of instruments, and step (b) includes graphic extrapolation.

4. The method according to claim 1 cyclically carried out with cycle periods in continuous freeze-drying plants comprising, heating plates, an entry chamber and an exit chamber wherein the method is employed in the exit chamber by adjusting at least one of the cycle periods of the plant and the temperature profile of the heating plates so that the product reaches a desired residual moisture content in the exit chamber.

5. The method according to claim 1, carried out in intermittently operating freeze-drying plants comprising a freeze-drying chamber having adjustable plates wherein the method is employed in the freeze-drying chamber by adjusting the duration of the secondary drying phase and the temperature of the adjustable plates so that at the end of the secondary drying phase the product attains a desired residual moisture content.

6. A device for the execution of the method according to claim 1 comprising:
   a vacuum measuring instrument,
   a shut-off device between a drying chamber and an ice condenser, and a programmable computer having a display panel on which the residual moisture is registered.

7. The method according to claim 1 wherein the preselected amount is a desorption rate zero point.

8. The method according to claim 1 wherein said step of measuring is carried out at ten-minute intervals of time.

9. A method for determining residual moisture content of dry product during a secondary drying phase in a freeze-drying plant having a freeze-drying chamber, condenser and a shut-off device located between the chamber and the condenser, the method comprising:

(a) closing the shut-off device for a preselected period of time;

(b) measuring a pressure change in the chamber;

(c) calculating a desorption rate from the shut-off time period of step (a), the chance in pressure measured in step (b), and a volume of the chamber;

(d) repeating steps (a)–(c) to calculate at least two desorption rates at regular intervals of time;

(e) from the at least two desorption rates, projecting a target time when the desorption rate will reach a target desorption rate, which target desorption rate alters a desired residual moisture content by only a preselected amount; and (f) integrating the calculated desorption rate from the target time back to a time of calculating the desorption rate in step (c) to determine a current residual moisture content of the drying product.

10. The method of claim 9 wherein the shut-off device is closed for thirty to sixty seconds.

11. The method of claim 9 wherein step (d) is repeated at ten-minute intervals.

12. An apparatus for determining residual moisture content of dry product during a secondary drying phase in a freeze-drying plant having a freeze-drying chamber and condenser, which apparatus comprises:

(a) a shut-off device located between the freeze-drying chamber and the condenser, the shut-off device including:

(i) a means for closing off the chamber and the condenser during specified, periods of time; and (ii) a means for measuring a chance in pressure in the chamber;

(b) a programmable computer having a display panel for displaying the residual moisture content, the computer including:

(i) a means for calculating at least two desorption rates from a volume of the chamber, the chance in pressure in the chamber, and the period of time the condenser and the chamber are closed off;

(ii) a means for storing a point in time when each of the desorption rates is calculated;

(iii) a means for calculating a target time from the at least two desorption rates, the target time being a time when the desorption rate is projected to reach a preselected near zero point; and (iv) without determining mass at the preselected near zero point, means for integrating the calculated desorption rate from the target time back to a point in time when the desorption rate was calculated to determine the residual moisture content.

* * * * *